United States Patent
Busson

(10) Patent No.: US 6,333,443 B1
(45) Date of Patent: Dec. 25, 2001

(54) PROCESS FOR THE PRODUCTION OF METHYLACETYLENE AND PROPADIENE

(75) Inventor: Christian Busson, Charbonniere (FR)

(73) Assignee: Institut Francais du Petrole (FR)

( * ) Notice: Subject to any disclaimer, the term of this patent is extended or adjusted under 35 U.S.C. 154(b) by 0 days.

(21) Appl. No.: 09/540,883

(22) Filed: Mar. 31, 2000

(30) Foreign Application Priority Data

Mar. 31, 1999 (FR) .................................................. 99 04124

(51) Int. Cl.$^7$ ................................ C07C 4/04; C07C 4/02
(52) U.S. Cl. ................... 585/539; 585/534; 585/601; 585/613
(58) Field of Search .................... 585/534, 539, 585/601, 613

(56) References Cited

U.S. PATENT DOCUMENTS

| | | | |
|---|---|---|---|
| 5,160,501 | * 11/1992 | Alagy et al. | 585/500 |
| 5,321,191 | * 6/1994 | Alagy et al. | 585/648 |
| 5,365,005 | * 11/1994 | Weill et al. | 585/500 |
| 5,554,347 | * 9/1996 | Busson et al. | 422/204 |
| 5,976,352 | * 11/1999 | Busson et al. | 208/75 |

FOREIGN PATENT DOCUMENTS

| | | |
|---|---|---|
| 0 733 609-A1 | * 9/1996 | (EP) . |
| 1 389 102 A | 6/1965 | (FR) . |
| 2 732 014 A | 9/1996 | (FR) . |

* cited by examiner

*Primary Examiner*—Walter D. Griffin
(74) *Attorney, Agent, or Firm*—Millen, White, Zelano & Branigan, P.C.

(57) ABSTRACT

A process for producing methylacetylene and propadiene in a reaction zone which is elongate in one direction (one axis) comprises a heating zone and a cooling zone following said heating zone, in which a gas mixture comprising at least one hydrocarbon containing at least three carbon atoms e.g. propane and/or propylene from stream cracking, and at least one diluent is circulated in the heating zone, under super-atmospheric pressure, in a flow direction substantially parallel to the direction (to the axis) of the heating zone, wherein the heating zone comprises at least one preheating zone in which the temperature of said gas mixture increases by about 50° C. to 120° C. per ¹/₁₀ of the length of the heating zone, at least one pyrolysis zone for the feed in which the temperature rises by about 20° C. to 50° C. per ¹/₁₀ of the length of the heating zone and at least one methylacetylene-propadiene formation zone in which the temperature climbs by about 70° C. to 150° C. per ¹/₁₀ of the length of the heating zone, the products formed at the end of the heating zone being cooled in the cooling zone then recovered at the of the reaction zone.

16 Claims, 4 Drawing Sheets

PROCESS FOR THE PRODUCTION OF METHYLACETYLENE AND PROPADIENE

The invention relates to a process for producing methylacetylene and propadiene by thermal conversion of a feed comprising at least one hydrocarbon containing at least three carbon atoms per molecule.

The synthesis of methylacetylene and propadiene is known to the skilled person. It is usually carried out by pyrolysis of propylene and/or isobutene or from propane, butane, but-1-ene or a mixture of but-2-ene isomers. French patent application FR-A-2 732014 describes a process for thermal conversion of saturated or unsaturated aliphatic hydrocarbons to acetylenic hydrocarbons. Said process is particularly applicable to the production of acetylene or methylacetylene but it does not describe propadiene formation.

U.S. Pat. No. 5,321,191 describes a process for thermal pyrolysis of hydrocarbons containing at least two carbon atoms. The process is intended for the production of light olefins, in particular ethylene and propylene.

European patent application EP-A-0 323 287, and U.S. Pat. Nos. 5,160,501 and 5,365,005 describe a process for thermal conversion of methane to hydrocarbons with a higher molecular weight, and a reactor for carrying out the process.

U.S. Pat. No. 5,554,347 describes an apparatus comprising a reactor for carrying out reactions such as pyrolysis. That reactor comprises heat exchange means which are supplied with a gas or a gas mixture.

The patent applications cited above use a reactor comprising heating means which are surrounded by sheaths of ceramic material. Those means are supplied with either electrical energy, or with gas so as to heat the feed, to carry out the conversion. The reactor is similar to that used in the present application.

One advantage of the invention is that it can be used to carry out thermal conversion of a feed while controlling the temperature during decomposition, which is currently not possible with conventional steam cracking reactors. The process of the invention enables temperature profiles to be defined. It defines a heating zone divided into three portions in which controlled temperature increases are implemented.

The invention provides a process for producing methylacetylene and propadiene in a reaction zone which is elongate in one direction (one axis) comprises a heating zone and a cooling zone following said heating zone, in which a gas mixture comprising at least one hydrocarbon containing at least three carbon atoms and at least one diluent is circulated in the heating zone, at an absolute pressure which is above atmospheric pressure, in a flow direction substantially parallel to the direction (to the axis) of the heating zone, said process being characterized in that the heating zone comprises at least one pre-heating zone in which the temperature of said gas mixture increases by about 50° C. to 120° C. per 1/10 of the length of the heating zone, at least one zone for pyrolysis of the feed in which the temperature rises by about 20° C. to 50° C. per 1/10 of the length of the heating zone and at least one methylacetylene-propadiene formation zone in which the temperature rises from about 70° C. to 150° C. per 1/10 of the length of the heating zone, the products formed at the end of the heating zone being cooled in the cooling zone then recovered at the end of the reaction zone.

In a particular implementation of the process of the invention, the heating zone comprises at least two banks substantially parallel to the axis separated by a non fluid tight partition of refractory material between two successive banks, each bank comprising a plurality of heating means disposed in at least one layer of heating elements and surrounded by sheaths of ceramic material which are substantially parallel to each other and substantially perpendicular to the axis of the heating zone.

The hydrocarbon-containing feeds used in the present invention comprise hydrocarbons containing at least three carbon atoms per molecule. Non limiting examples are saturated aliphatic hydrocarbons such as propane and alkane mixtures (LPG) or unsaturated hydrocarbons such as propylene and butenes, mixtures of alkanes and alkenes such as propane and propylene, $C_3$, $C_4$ and $C_5$ cuts produced by fluidised bed catalytic cracking, steam cracking, alkane dehydration and by isomerisation of olefins or by dimerisation.

The feed preferably contains essentially propylene and/or propane and originates from steam cracking.

Under normal pressure and temperature conditions, the feeds are gas mixtures which also comprise at least one diluent. Said diluent is normally selected from the group formed by steam and nitrogen. Preferably, steam is used. The weight ratio of the diluent to the hydrocarbon feed is normally about 0.1:1 to 5:1, preferably about 0.5:1 to 2.5:1. Before being introduced into the heating zone, the gas mixture is pre-heated to a temperature in the range about 100° C. to 650° C. It is then introduced parallel to the axis of the heating zone.

The heating zone is formed from at least one pre-heating zone, at least one pyrolysis zone and at least one methylacetylene-propadiene formation zone. It is usually heated by heating means which are surrounded by a sheath, so as to form heating elements.

Said heating elements provide the heat necessary to initiate the pyrolysis reaction. The total number of said elements in the heating zone is fixed by the operator. It essentially depends on the nature of the feed to be converted and on the size of the apparatus.

The characteristics of the heating elements, their number, the distance separating them and their configuration are, for example, described in the patent documents U.S. Pat. No. 5,554,347 and EP-A-0 323 287. The heating elements are supplied with energy by any means known to the skilled person. Usually, they are supplied with electrical or gas heating, preferably gas, either in isolation or in small groups such that they define heating sections along the heating zone. They can thus modulate the quantity of energy provided along this zone. They can thus establish a thermal profile. The heating zone is normally composed of 2 to 20 heating sections, preferably 3 to 12 sections.

Said zone can also comprise means for controlling and modulating the heating such as those described, for example, in patent documents EP-A-0 323 287 and U.S. Pat. No. 5,554,347.

The heating means can be electrical resistors surrounded by sheaths and heated by electrodes, such as those described in patent documents EP-A-0 323 287 and U.S. Pat. No. 5,160,501, or they can be constituted by sheaths containing a gas burner, as described in patent U.S. Pat. No. 5,554,347.

The heating elements form layers which are substantially parallel to the axis of the heating zone. This then defines banks, each comprising at least one layer of heating elements. Each bank is substantially parallel to the axis of the heating zone. The banks are separated by non fluid tight partitions of ceramic material. Said partitions have adapted shapes, which can create zones of turbulence inside the banks, to encourage the pyrolysis reaction and the methylacetylene-propadiene formation.

The sheaths surrounding the heating means are usually of ceramic material. They can be disposed in a superimposed or staggered manner and can form an array with a triangular, square or rectangular pattern in transverse projection. In the case of electrical resistors, patent U.S. Pat. No. 5,160,501 demonstrates that it is not in any way necessary to have a perfect seal in the sheaths, so as to allow at least a portion of a sheath gas G, contained in the space formed by said sheaths and the resistors, to diffuse. The gas G contains hydrogen and/or stream and/or carbon monoxide and/or an inert gas, which can diffuse from the interior to the exterior of the sheaths without disturbing the pyrolysis reaction. It is then diluted in the gas mixture. Said sheaths have also been described in the patent applications cited above.

The total residence time for the feed in the heating zone is normally in the range about 12 to 2000 milliseconds (ms), preferably between about 56 and 1500 ms and more particular it about 111 to 1100 ms. The absolute pressure is generally higher than atmospheric pressure. It is usually higher, at more than 1.1 bars (0.11 MPa), preferably in the range about 1.1 bars to 10 bars (0.11 to 1 MPa), more preferably between about 1.2 and 5 bars (0.12 to 0.5 MPa).

Said heating zone is formed from a first feed pre-heating zone. The pre-heating means are heated such that the temperature of the gas mixture climbs by about 50° C. to 120° C. per 1/10 of the length of the heating zone. The outlet temperature from said zone is the minimum temperature for pyrolysis of the feed.

The pyrolysis zone can convert at least a portion of the feed. The residence time for said feed in the pyrolysis zone is normally about 10 to 1000 ms, preferably about 50 to 900 ms, more preferably about 100 to 700 ms. The energy supplied to the heating sections is modulated such that the temperature rise in the pyrolysis zone is normally about 20° C. to about 50° C. per 1/10 of the length of the heating zone.

The methylacetylene-propadiene formation zone operates at high temperature. The residence time for the gas mixture must be short to avoid the formation of by-products. It essentially depends on the nature of the feed to be converted. It is generally in the range about 1 to 400 ms, usually in the range about 5 to 300 ms and more preferably in the range about 10 to 200 ms. As a general rule, it is shorter than that of the pyrolysis zone. The energy supplied to different heating sections is modulated such that the temperature rise in the methylacetylene-propadiene formation zone is generally in the range about 70° C. to 150° C. per 1/10 of the length of the heating zone. The final temperature at the outlet from the heating zone is normally in the range about 80° C. to 130° C., preferably in the range about 90° C. to 110° C.

The heating zone is followed by a cooling (chilling) zone so as to rapidly reduce the temperature of the effluents obtained from the heating zone. In the case of a direct chill, the effluents are rapidly brought into contact with a cooling fluid (chilling agent) which is well known to the skilled person. The fluid is generally injected into the effluents using injectors, usually of ceramic material, located at the periphery of the heating zone and connected to an external supply of chilling fluid. The effluent gases are recovered via an outlet orifice at the end of the reaction zone.

In the case of indirect chilling, the effluents can be partially cooled by circulation through gas tight conduits disposed in the cooling zone via which the chilling agent flows, these conduits being connected to the external source of the chilling agent.

The process of the invention is normally carried out in an apparatus comprising a reactor (1) of elongate form along one axis, preferably with a square or rectangular cross section, comprising at a first end means (5) for supplying a gas mixture, comprising at least one hydrocarbon containing at least three carbon atoms, and at the opposite end evacuation means (8) for the effluents produced and heating means then cooling means between these two ends. Said reactor comprises at least two banks substantially parallel to the reactor axis, separated by a non fluid tight partition (9) of refractory material between these two banks. Each bank comprises a plurality of heating means (3), said means being disposed in layers of heating elements and surrounded by sheaths (4) of ceramic material substantially parallel to each other and substantially perpendicular to the reactor axis, so as to define spaces or passages for circulating gas mixtures and/or effluents between the sheaths and/or banks which are formed. Said heating means and said sheaths are adapted to heat said passages by successive independent transverse sections which are substantially perpendicular to the reactor axis. Said reactor comprises heating control and modulation heating means connected to said heating means. It also comprises means (7) for cooling effluents, connected to said means for supplying cooling fluid.

In a particular implementation of the process of the invention, said reactor can be preceded by a steam cracker. This apparatus has been described in patent application FR-A-2 748 273. It enables the reactor to be continuously decoked.

The steam cracker comprises at least two steam cracking tubes, each tube being connected to one end of a feed supply line. Said supply lines are controlled by regulating valves. These valves allow the gas mixture (comprising the hydrocarbon feed and a fluid essentially formed by steam) to circulate in certain tubes of the steam cracker, and allow a fluid alone formed essentially by steam to circulate in other tubes. The gas mixture from the steam cracker tubes containing the cracking products then circulates in at least one bank of the pyrolysis reactor, and the fluid formed essentially of water vapour circulates in at least one other bank so as to carry out decoking. Valves enable the pyrolysis and decoking steps to be alternated in each bank of the pyrolysis reactor.

Regarding cooling, the products formed and the decoking effluent can be mixed before being introduced into the cooling zone. They can also be separately cooled in their respective banks located in the cooling zone, and then can optionally be mixed.

The invention will be better understood from the description of different implementations which are given by way of non limiting example

DETAILED DESCRIPTION OF THE DRAWINGS

Figure 1:
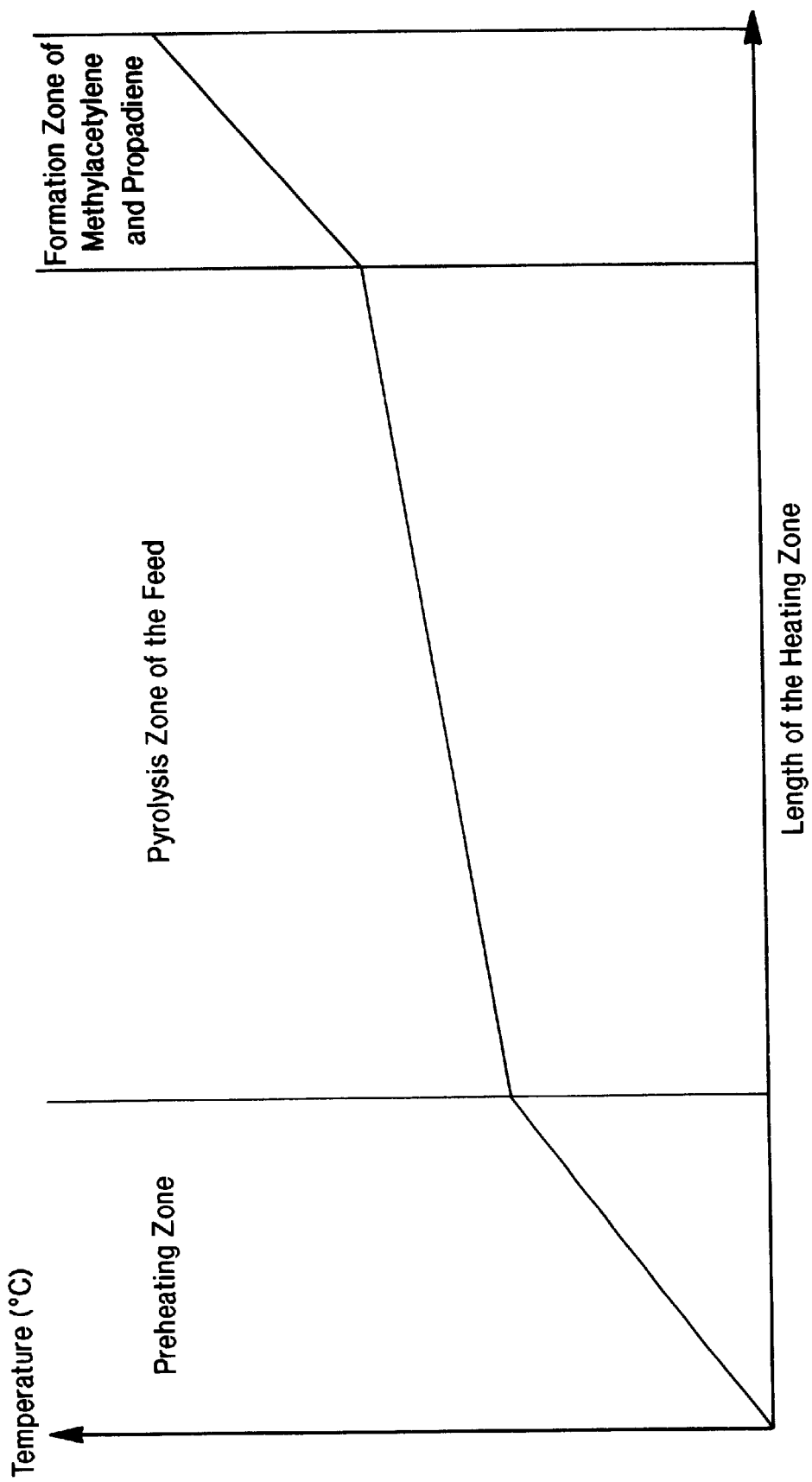
FIGS. 1, 3 and 4 are temperature profiles as a function of the length of heating zones.

FIG. 1 illustrates a theoretical temperature profile for any feed in the heating zone. Said profile is expressed as a function of temperature (° C.) and the length of the heating zone. The heating zone is heated so as to produce a controlled temperature rise in each of the three successive zones. The ideal temperature variation curve in each zone is represented by a straight line. The inclination (slope) of each straight line depends on the nature of the feed to be cracked. The heating means enables the temperature increase in each zone to be regulated.

Figure 2:
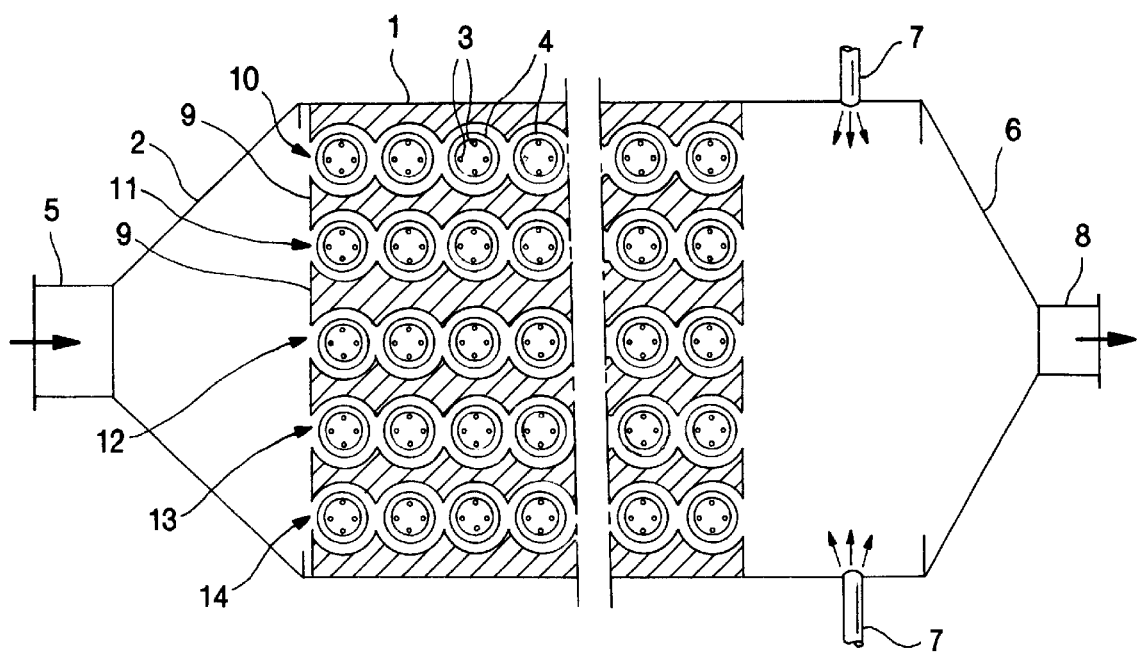
FIG. 2 is a schematic drawing of a reactor.

FIG. 2 shows one implementation in which a substantially horizontal reactor (1) which is elongate in form and of rectangular cross section comprises a distributor (2) which can supply the reactor with reaction gas mixture via an inlet orifice (5). This reaction gas mixture, which contains a mixture of steam and at least one hydrocarbon containing at least three carbon atoms per molecule, has been pre-heated in conventional manner, preferably by convection, in a zone which is not shown in the figure.

The reactor comprises banks (10 to 14) separated from each other by partitions (9), which are non fluid tight and of ceramic material, with a shape including cells adapted to encourage turbulence inside the bank and thus to encourage the reaction. These banks are substantially parallel to each other and substantially perpendicular to the axis of reactor (1) defined along the direction of flow of the feed.

Each bank (10 to 14) comprises a plurality of heating means (3) surrounded by sheaths (4), disposed in parallel layers and forming a square patterned array in one plane (the plane of the Figure). In the case of electrical heating, these sheaths can contain a plurality of electrical resistors (3) bathed in a sheath gas G.

Said layers define transverse heating sections which are substantially perpendicular to the axis of reactor(1).

The supply to the heating sections is not shown in the Figure. In the case of electrical heating, these are pairs of electrodes. In the case of gas heating, the sections are supplied by circulating a gas or a mixture of gases. In both cases, pyrometric probes ensure automatic regulation of the temperature of each heating section, by a conventional regulation means which is not shown in the Figure.

In the first portion of the heating zone, the heating means are heated so that the temperature increases by about 50° C. to 120° C. per 1/10 of the length of the heating zone. The gas mixture is pre-heated, so that its temperature is brought to the minimum feed pyrolysis temperature.

The gas mixture then circulates in the pyrolysis zone. The heating sections are modulated so that the temperature rises by about 20° C. to about 50° C. per 1/10 of the length of the heating zone.

The cracked feed then arrives at the methylacetylene-propadiene formation zone, where the temperature rises by about 70° C. to 150° C. per 1/10 of the length of the heating zone.

The effluents are cooled in a cooling zone (6). They are brought into contact with a chilling agent introduced via chilling injectors (7) disposed at the periphery of reactor (1) and connected to an external source of a chilling agent, not shown in the Figure. The effluent gases are cooled to 500° C. then recovered at the end of reactor (1) via an outlet orifice (8).

EXAMPLE

Example 1

A horizontal indirect chill reactor was used, with heating means which were silicon carbide Crusilite type electrical resistors from KANTHAL. These resistors were surrounded by sintered silicon carbide sheaths, disposed concentrically with respect to the centre of the circle surrounding the resistors.

These sheaths, 9 in all, were disposed in a line perpendicular to the direction of feed circulation (vertically). Each resistor was 100 mm long with a diameter of 10 mm. The ceramic sheaths were 110 mm long, with an external diameter of 50 mm and an internal diameter of 42 mm. The distance separating two neighbouring sheaths or a sheath and a wall of the reactor of refractory concrete was 5 mm.

The temperature of the gas along the reactor was regulated thermally by means of thermocouples disposed in the spaces in which the feed circulated.

The feed was 99.7% pure propylene diluted with water in a water/feed weight ratio of 1. The feed was pre-heated in conventional manner to 450° C.

The following temperature profile was imposed:

| Sheath | Temperature (° C.) | Temperature rise (° C. per 1/10 of length of heating zone) | Residence time (ms) and absolute pressure (MPa) |
|---|---|---|---|
| 1 to 2 | 450–670 | 110.0 | 22 ms; 0.15 MPa |
| 3 to 7 | 670–860 | 31.6 | 55 ms; 0.15 MPa |
| 8 to 9 | 860 to 1030 | 85.0 | 22 ms; 0.15 MPa |

Figure 3:
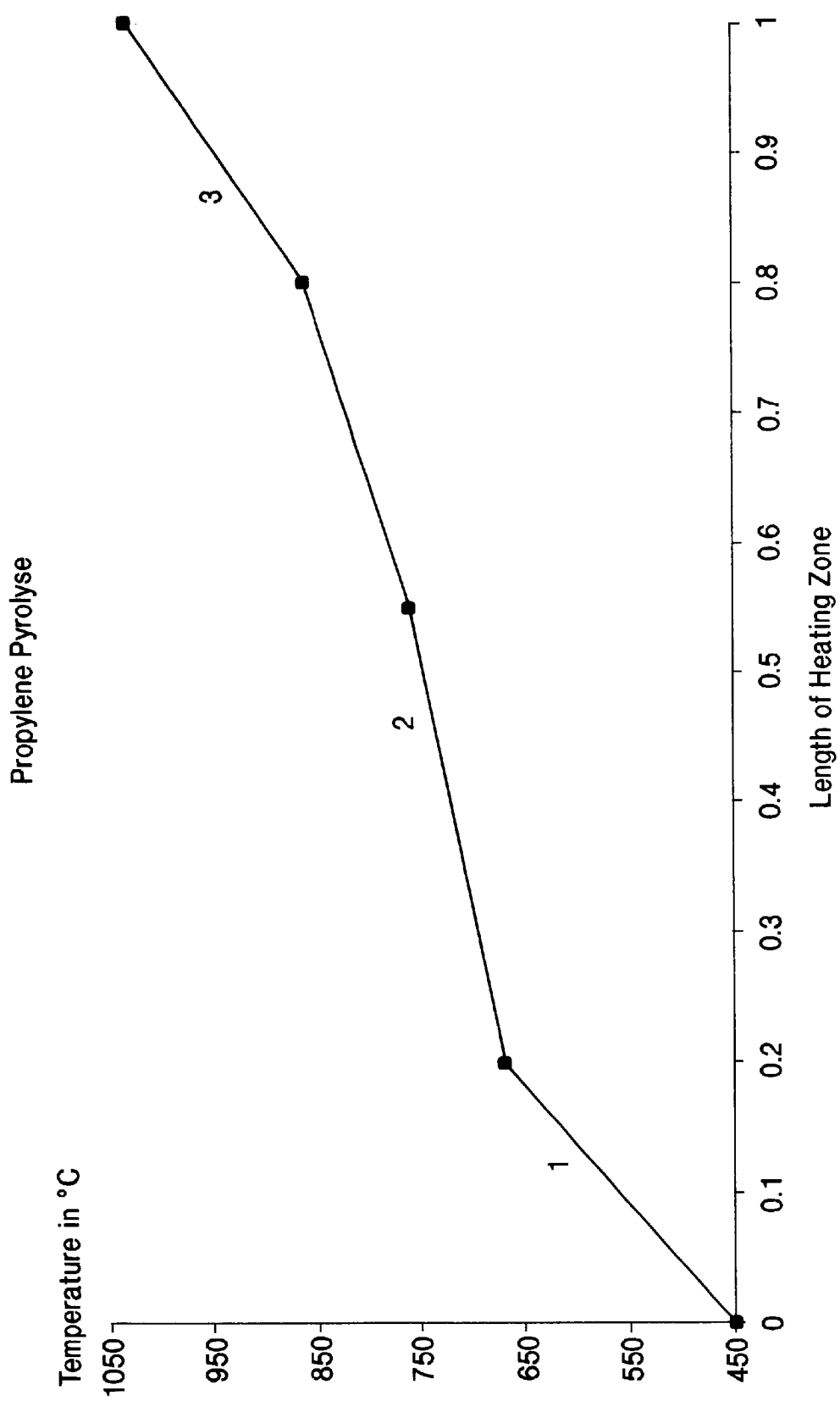

Thus there were three temperature rise zones, as shown on FIG. 3 in curves 1, 2 and 3 respectively. Curve 1 shows the temperature rise in the pre-heating zone; curve 2 shows the temperature rise in the pyrolysis zone; and curve 3 shows the temperature rise in the methylacetylene-propadiene formation zone.

The effluent gases were rapidly cooled, firstly to 500° C. by indirect exchange, then other temperature exchangers to then reduce their temperature to ambient temperature.

Under these conditions, the degree of propylene conversion was 60.5%.

The selectivities* of the principal products were as follows:

| Products | Selectivity (%) |
|---|---|
| Methane | 16.1 |
| Ethylene | 36.4 |
| Methylacetylene | 8.2 |
| Propadiene | 12.4 |
| Acetylene | 3.2 |
| Benzene | 8.8 |

The selectivity of product P equals the number of carbon atoms of product P multiplied by 100 and divided by the number of carbon atoms of propylene converted.

Example 2

The reactor used was similar to that used in Example 1 but comprised 21 heating units.

The feed used was 99.5% pure propane diluted with water in a steam/feed ratio of 1. It was conventionally pre-heated to 450° C.

The following temperature profile was imposed:

| Sheath | Temperature (° C.) | Temperature rise (° C. per 1/10 of length of heating zone) | Residence time (ms) and absolute pressure (MPa) |
| --- | --- | --- | --- |
| 1 to 5 | 450–670 | 91.6 | 147 ms; 1.5 bars |
| 6 to 17 | 670–860 | 33.9 | 353 ms; 1.5 bars |
| 18 to 21 | 860–1050 | 100.0 | 120 ms; 1.5 bars |

Figure 4:
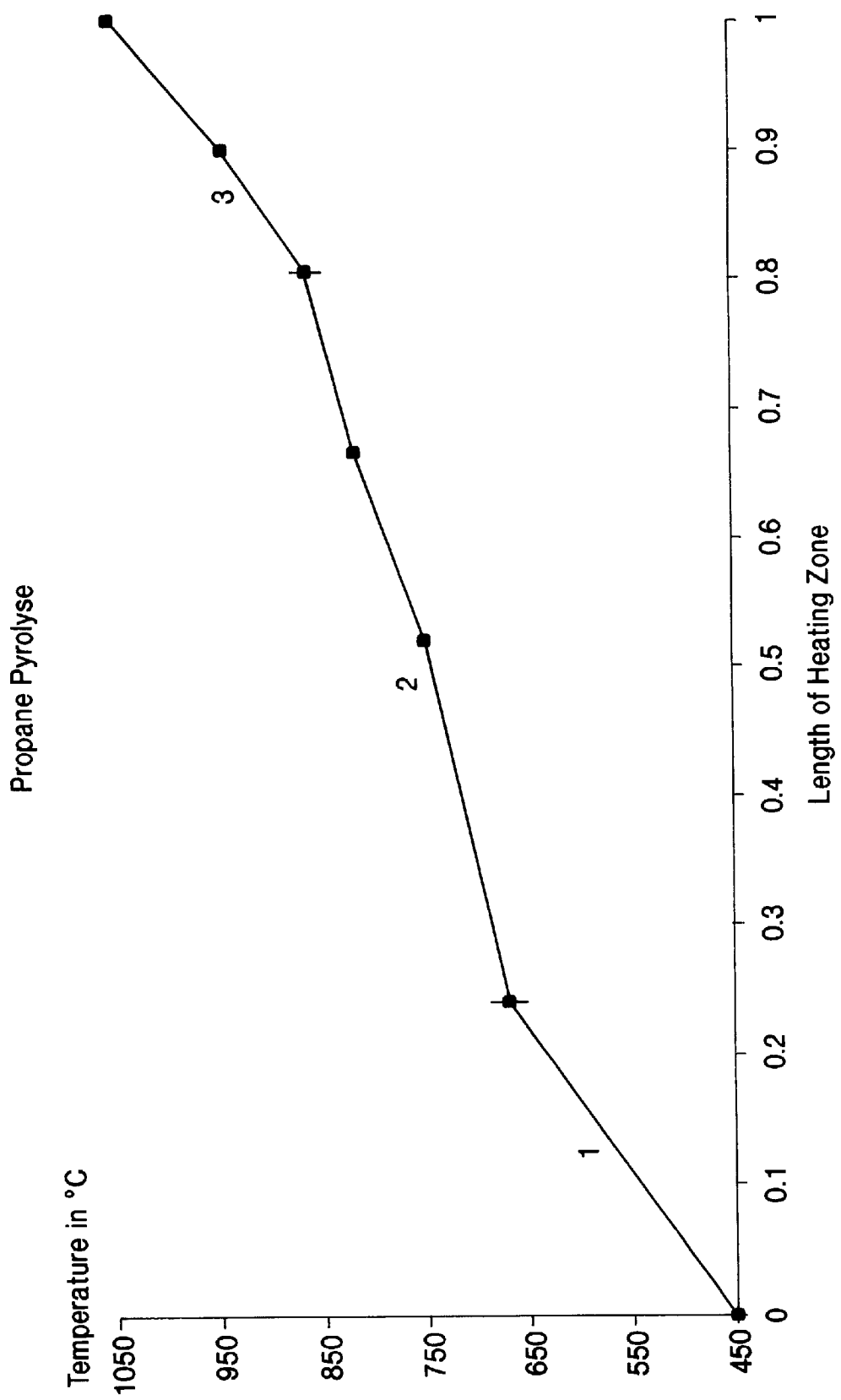

There were three temperature rise zones, as shown in FIG. 4 by curves 1, 2 and 3 respectively.

Under these conditions, the degree of propane conversion was 98.5%.

The selectivities of the principal products were as follows:

| Products | Selectivity (%) |
| --- | --- |
| Methane | 19.7 |
| Ethylene | 41.0 |
| Methylacetylene | 9.9 |
| Propadiene | 9.9 |
| Acetylene | 3.1 |
| Benzene | 4.1 |
| Propylene | 8.3 |

What is claimed is:

1. A process for producing methylacetylene and propadiene in a reaction zone which is elongate in one direction (one axis), comprising a heating zone and a cooling zone following said heating zone, said process comprising circulating a gas mixture comprising at least one hydrocarbon containing at least three carbon atoms and at least one diluent in the heating zone having a total residence time for the gas mixture in the heating zone in the range of about 12 to 2000 milliseconds (ms), at an absolute pressure which is above atmospheric pressure, in a flow direction substantially parallel to the direction (to the axis) of the heating zone, wherein the heating zone comprises in succession at least one pre-heating zone in which the temperature of said gas mixture increases by about 50° C. to 120° C. per ¹/₁₀ of the length of the heating zone, at least one zone for pyrolysis in which the temperature rises further by about 20° C. to 50° C. per ¹/₁₀ of the length of the heating zone and at least one methylacetylene-propadiene formation zone in which the temperature rises further by about 70° C. to 150° C. per ¹/₁₀ of the length of the heating zone, wherein the residence time for the gas mixture in the methylacetylene-propadiene formation zone is shorter than the residence time for the gas mixture in the pyrolysis zone; and the residence time for the gas mixture in the pyrolysis zone is in the range of about 10 to 1000 ms, the products formed at the end of the heating zone being cooled in the cooling zone then recovered at the end of the reaction zone.

2. A process according to claim 1, in which the diluent is steam or nitrogen.

3. A process according to claim 1, in which the weight ratio of the diluent to the at least one hydrocarbon is in the range of about 0.1:1 to 5:1.

4. A process according to claim 1, in which the final temperature at the outlet from the heating zone is in the range of about 800° C. to 1300° C.

5. A process according to claim 1, in which the absolute pressure is more than 1.1 bars (0.11 MPa).

6. A process according to claim 1, in which the residence time for the gas mixture in the methylacetylene-propadiene formation zone is in the range of about 1 to 400 ms.

7. A process according to claim 1, in which the heating zone comprises at least two banks substantially parallel to the axis separated by a non fluid tight partition of refractory material between two successive banks, each bank comprising a plurality of heating means disposed in at least one layer of heating elements and surrounded by sheaths of ceramic material which are substantially parallel to each other and are substantially perpendicular to the axis of the heating zone.

8. A process according to claim 2, in which the weight ratio of the diluent to the at least one hydrocarbon is in the range of about 0.1:1 to 5:1.

9. A process according to claim 8, in which the final temperature at the outlet from the heating zone is in the range of about 800° C. to 1300° C.

10. A process according to claim 9, in which the absolute pressure is more than 1.1 bars (0.11 MPa).

11. A process according to claim 10, in which the total residence time for the gas mixture in the heating zone is in the range of about 12 to 2000 milliseconds (ms).

12. A process according to claim 11, in which the residence time for the gas mixture in the methylacetylene-propadiene formation zone is shorter than the residence time for the gas mixture in the pyrolysis zone.

13. A process according to claim 12, in which the residence time for the gas mixture in the pyrolysis zone is in the range of about 10 to 1000 ms.

14. A process according to claim 13, in which the residence time for the gas mixture in the methylacetylene-propadiene formation zone is in the range of about 1 to 400 ms.

15. A process according to claim 14, in which the heating zone comprises at least two banks substantially parallel to the axis separated by a non fluid tight partition of refractory material between two successive banks, each bank comprising a plurality of heating means disposed in at least one layer of heating elements and surrounded by sheaths of ceramic material which are substantially parallel to each other and are substantially perpendicular to the axis of the heating zone.

16. A process according to claim 1 wherein said at least one hydrocarbon containing at least three carbon atoms is a propylene.

* * * * *